United States Patent [19]

Duke, Jr. et al.

[11] Patent Number: 5,290,764
[45] Date of Patent: Mar. 1, 1994

[54] STABILIZATION OF ACTIVE PLASMINOGEN ACTIVATOR INHIBITOR-1

[75] Inventors: Jodie L. Duke, Jr., Newark; Harry L. Walton, Jr.; Thomas M. Reilly, both of Wilmington, all of Del.

[73] Assignee: The Dupont Merck Pharmaceutical Company, Wilmington, Del.

[21] Appl. No.: 820,523

[22] Filed: Jan. 14, 1992

[51] Int. Cl.$^5$ ............... A61K 37/00; A61K 35/14
[52] U.S. Cl. .................. 514/21; 514/27; 514/822; 530/380; 530/381; 530/382; 530/350; 530/395; 530/402; 530/427
[58] Field of Search ............ 514/21, 27, 822; 530/380, 381, 382, 350, 395, 402, 407, 427

[56] References Cited

U.S. PATENT DOCUMENTS

| 4,806,524 | 2/1989 | Kawaguchi et al. | 530/395 |
| 5,112,955 | 5/1992 | Wun | 530/350 |

OTHER PUBLICATIONS

Arakawa et al, *Biochemistry*, vol. 21, No. 25, pp. 6536-6544, 1982.
Reilly et al, *Chemical Abstracts*, vol. 115, p. 589, Ref. #253188d., 1991.
Chandler et al., *Clin. Chem.* vol. 35, No. 5, pp. 787-793, 1989.
Rauby et al, *Thrombosis and Haemostasis*, vol. 62, No. 3, 917-922, 1989.
Ehrlich et al, *Biochemistry*, vol. 30, No. 4, pp. 1021-1028, 1991.
Medvescek et al, *Chemical Abstracts*, vol. 114, p. 527, Ref. #5255u., 1991.
Stump et al., *Semin. Thromb. Hemos.*, vol. 16, No. 3, pp. 260-273 (1990).
Lijnen et al., *Fibrinolysis*, vol. 3, pp. 67-77 (1989).
Van Mourik et al., *J. Biol. Chem.*, vol. 259, pp. 14914-14921 (1984).
Colucci et al., *J. Clin. Invest.*, vol. 75, pp. 818-824 (1985).
Almer et al., *Thromb. Research*, vol. 47, pp. 335-339 (1987).
Hamsten et al., *New England J. of Medicine*, vol. 313, pp. 1557-1563 (1985).
Wiman et al., *J. Lab. Clin. Med.*, vol. 105, pp. 265-270 (1985).
Colucci et al., *J. Clin. Invest.*, vol. 78, pp. 138-144 (1986).
Ehrlich et al., *J. Biol. Chem.*, vol. 265, pp. 13029-13035 (1990).
Reilly et al., *J. Biol. Chem.*, vol. 265, No. 16, pp. 9570-9574 (1990).
Racanelli et al., *Fibr.*, vol. 4, Suppl. 3, p. 43 (1990).
Vaughan et al. *J. Clin. Invest.*, vol. 84, pp. 586-591 (1989)
Cramer et al., *Blood*, vol. 77, No. 4, pp. 694-699 (1991).
Timasheff et al., "Stabilization of Protein Structure By Solvents", in *Protein Structure: A Practical Approach*, T. E. Creighton, ed., IRL Press (1989).
Volkin et al., "Minimizing Protein Inactivation", in *Protein Function: A Practical Approach*, T. E. Creighton, ed., IRL Press (1989).
Keijer et al., *Fibrinolysis*, vol. 4, pp. 153-159 (1990).
Coleman et al., *J. Biol. Chem.*, vol. 257, pp. 4260-4264 (1982).
Kruithof et al., *Thromb. Haemostasis*, vol. 59, pp. 7-12 (1988).
Booth et al., *Eur. J. Biochem.*, vol. 165, pp. 595-600 (1987).

(List continued on next page.)

*Primary Examiner*—Michael G. Wityshyn
*Assistant Examiner*—Abdel A. Mohamed

[57] ABSTRACT

Processes for stabilizing active PAI-1 protein comprising combining active PAI-1 protein with an aqueous buffer having an ionic strength of at least about 5 millisiemens and a sugar selected from the group consisting of monosaccharides and disaccharides, and/or subjecting the active PAI-1 protein to lyophilization, are disclosed. Also described are compositions, including pharmaceutical compositions and kits, which include the stabilized active PAI-1 protein, and therapeutic processes employing the same in the treatment of fibrinolysis.

12 Claims, No Drawings

OTHER PUBLICATIONS

Andreasen et al., *J. Biol. Chem.*, vol. 261, pp. 7644–7651 (1986).
Zeheb et al., *Thromb. Haemostasis*, vol. 58, pp. 1017–1023 (1987).
Hekman et al., *J. Biol. Chem.*, vol. 260, pp. 11581–11587 (1985).
Lambers et al., *J. Biol. Chem.*, vol. 262, pp. 17492–17496 (1987).
Ginsburg et al., *J. Clin. Invest.*, vol. 78, pp. 1673–1680 (1986).
Ny et al., *Proc. Natl. Acad. Sci.* U.S.A., vol. 83, pp. 6776–6781 (1986).
Pannekoek et al., *EMBO J.* vol. 5, pp. 2539–2544 (1986).
Wun et al., *FEBS Lett.*, vol. 210, pp. 11–16 (1987).
Alessi et al., *Eur. J. Biochem.*, vol. 175, pp. 531–540 (1988).
Andreasen et al., *FEBS Lett.*, vol. 209, pp. 213–218 (1986).
Sisk et al., *Gene (Amst.)*, vol. 96, pp. 305–309 (1990).
Remington's, *Pharmaceutical Sciences*, Gennaro, A. R., ed., Mack Publishing Co., Easton, Pa. (1990) pp. 1435–1712.
*The United States Pharmacopeia*–The National Formulary, 22nd Revision, Mack Printing Company, Easton, Pa. (1990) pp. 1857–1859.
Coleman, *J. Biol. Chem.*, vol. 261, pp. 4352–4357 (1986).
Lambers et al., *Fibrinolysis*, vol. 2, Supp. 1, p. 33 (1988).
Kooistra et al., *Biochem. J.*, vol. 239, pp. 497–503 (1989).
Franke et al., *Biochem. Biophys. Acta.*, vol. 1037, pp. 16–23 (1990).

STABILIZATION OF ACTIVE PLASMINOGEN ACTIVATOR INHIBITOR-1

BACKGROUND OF THE INVENTION

Human tissue-type plasminogen activator (tPA) is a key physiological regulator of fibrinolysis. It converts the zymogen plasminogen into plasmin, the enzyme which degrades the fibrin network of the thrombus. Apparently, in the presence of a clot, both tPA and plasminogen bind to fibrin and form a ternary complex in which plasminogen is efficiently activated. The affinity for fibrin makes tPA clot-specific, and useful as a therapeutic agent for fibrinolytic therapy in man. Stump et al., Semin. Thromb. Hemos., Vol. 16, No. 3. pp. 260-273 (1990); Lijnen et al., Fibrinolysis, Vol. 3, pp. 67-77 (1989).

The principal physiological regulator of tPA appears to be a specific, fast-acting, plasminogen activator inhibitor type-1 (PAI-1). PAI-1 is a protein of a molecular weight of about 50,000 which binds to tPA in a 1:1 complex, and inactivates it. Recent clinical studies suggest that elevated levels of PAI-1, by reducing the net endogenous fibrinolytic capacity, may contribute to the pathogenesis of various thrombotic disorders, including myocardial infarction, deep vein thrombosis, and disseminated intravascular coagulation. Van Mourik et al., J. Biol. Chem., Vol. 259, pp. 14914-14921 (1984); Colucci et al., J. Clin. Invest., Vol. 75, pp. 818-824 (1985); Almer et al., Thromb. Research, Vol. 47, pp. 335-339 (1987); Hamsten et al., New England J. of Medicine, Vol. 313, pp. 1557-1563 (1985); Wiman et al., J. Lab. Clin. Med., Vol 105, pp. 265-270 (1985).

Two forms of PAI-1 differing in tPA inhibitory activity and referred to as active and inactive or latent (inactive/latent) forms have been observed with PAI-1 protein from both natural and recombinant sources. Reilly et al., J. Biol. Chem., Vol. 265, No. 16, pp. 9570-9574 (1990); Lambers et al., Fibrinolysis, Vol. 2, Supp. 1, p. 33 (1988); Vaughan et al., J. Clin. Invest., Vol. 84, pp. 586-591 (1989). Considerable efforts have been directed to maximizing the amount of the active PAI-1 protein isolated, and researchers have achieved some success in this regard. For example, it has been reported that inactive/latent PAI-1 protein may be converted to an active form by treatment with denaturants such as sodium dodecylsulfate (SDS), guanidium hydrochloride and urea, or with negatively-charged phospholipids. Reilly et al., J. Biol. Chem., Vol. 265, No. 16, pp. 9570-9574 (1990); Vaughan et al., J. Clin. Invest., Vol. 84, pp. 586-591 (1989). Recombinant techniques have also been developed which yield substantial quantities of functionally active, E. coli-expressed, human PAI-1 protein. Reilly et al., J. Biol. Chem., Vol. 265, No. 16, pp. 9570-9574 (1990); Sisk et al., Gene (Amst.), Vol. 96, pp. 305-309 (1990); Davis et al., U.S. Ser. No. 350,264, filed May 11, 1989, entitled "High Level Expression of Functional Human Plasminogen Activator Inhibitor in E. coli". In addition, purification procedures have been discovered in which active PAI-1 may be separated from the inactive/latent form. Hayman et al., U.S. Ser. No. 671,433, filed Mar. 20, 1991, entitled "Purification of Active and Inactive/Latent Forms of Plasminogen Activator Inhibitor-1". Although some progress has been made in maximizing the amount of active PAI-1 protein, one problem which has not been fully addressed to date is the inherent instability of the PAI-1 active form. Indeed, it has been reported by researchers that active PAI-1 is rapidly converted following synthesis to a latent form by some unknown mechanism. Reilly et al., J. Biol. Chem., Vol. 265, No. 16, pp. 9570-9574 (1990); Kooistra et al., Biochem. J., Vol. 239, pp. 497-503 (1989). In view of the labile nature of the active form, some scientists have concluded that obtaining a pure sample of active PAI-1 is "an unrealistic goal". Franke et al., Biochim. Biophys. Acta, Vol. 1037, pp. 16-23 (1990).

Thus, although some success has been achieved in increasing the amount of active form PAI-1 obtained, means for stabilizing this active form and minimizing its conversion to inactive/latent PAI-1 are needed. The present invention is directed to this important end.

SUMMARY OF THE INVENTION

In one embodiment, the present invention is directed to processes for stabilizing active PAI-1 protein, such processes comprising combining active PAI-1 protein with an aqueous buffer having an ionic strength of at least about 5 millisiemens and a sugar selected from the group consisting of monosaccharides and disaccharides.

In another aspect, the present invention pertains to compositions comprising active PAI-1 protein in combination with an aqueous buffer having an ionic strength of at least about 5 millisiemens and a sugar selected from the group consisting of monosaccharides and disaccharides. The compositions may, if desired, be pharmaceutical compositions wherein the active PAI-1 protein is present an amount therapeutically effective to inhibit fibrinolysis in a mammal.

Also contemplated by the present invention are methods of treating fibrinolysis in mammals comprising administering to the mammal a pharmaceutical composition comprising active PAI-1 protein, in an amount therapeutically effective to inhibit fibrinolysis, in combination with an aqueous buffer having an ionic strength of at least about 5 millisiemens and a sugar selected from the group consisting of monosaccharides and disaccharides.

Pharmaceutical kits for the treatment of fibrinolysis in a mammal comprising a sterile container of a pharmaceutical composition comprising active PAI-1, in an amount therapeutically effective to inhibit fibrinolysis, in combination with an aqueous buffer having an ionic strength of at least about 5 millisiemens and a sugar selected from the group consisting of monosaccharides and disaccharides, and, if desired, other conventional pharmaceutical kit components, are also within the scope of the subject invention.

In still other embodiments, the present invention pertains to processes for stabilizing active PAI-1 protein comprising subjecting the active PAI-1 protein to lyophilization. The active PAI-1 protein may, if desired, further comprise a buffer having an ionic strength of at least about 5 millisiemens and a sugar selected from the group consisting of monosaccharides and disaccharides.

In further embodiments, the present invention contemplates stable active PAI-1 protein in lyophilized form, as well as active PAI-1 protein stabilized by lyophilization and then reconstituted.

Furthermore, the present invention contemplates pharmaceutical compositions comprising active PAI-1 protein stabilized by lyophilization and then reconstituted, in an amount therapeutically effective to inhibit fibrinolysis in a mammal, as well as methods of treating fibrinolysis in a mammal comprising administering to the mammal the foregoing pharmaceutical compositions.

Additionally, the subject invention is directed to pharmaceutical kits for the treatment of fibrinolysis in a mammal, the kits comprising a sterile container of active PAI-1 protein, in lyophilized form, in an amount therapeutically effective to inhibit fibrinolysis, and at least one sterile container of a reconstitution liquid. Also, the present invention contemplates pharmaceutical kits for the treatment of fibrinolysis in a mammal the kits comprising a sterile container of active PAI-1 protein stabilized by lyophilization and then reconstituted. The foregoing kits may also include, if desired, other conventional pharmaceutical kit components.

DETAILED DESCRIPTION OF THE INVENTION

In accordance with the present invention, active PAI-1 protein may be stabilized by combining it with a buffer having an ionic strength of at least about 5 millisiemens and a sugar selected from the group consisting of monosaccharides and disaccharides. Also in accordance with the present invention, active PAI-1 may be stabilized by subjecting it to lyophilization.

The phrase "PAI-1 protein", as used herein, denotes the protein commonly referred to as plasminogen activator inhibitor-1, either naturally or recombinantly produced. Naturally and recombinantly produced PAI-1 proteins are well known in the art, as evidenced by numerous publications directed to the same.

For example, naturally produced PAI-1 may isolated from human plasma or endothelial cell culture fluids, as discussed in Coleman et al., J. Biol. Chem., Vol. 257, pp. 4260–4264 (1982), Van Mourik et al., J. Biol. Chem., Vol. 259, pp. 14914–14921 (1984), Kruithof et al., Thromb. Haemostasis, Vol. 59, pp. 7–12 (1988), and Booth et al., Eur. J. Biochem., Vol 165, pp. 595–600 (1987), the disclosures of each of which are hereby incorporated herein by reference in their entirety. PAI-1 may also be isolated from such other natural sources as bovine aortic endothelial cells, HT 1080 human fibrosarcoma cells, and hepatoma tissue culture rat hepatoma cells, as discussed in Van Mourik et al., J. Biol. Chem., Vol. 259, pp. 14914–14921 (1984), Andreasen et al., J. Biol. Chem., Vol. 261, pp. 7644–7651 (1986), and Zeheb et al., Thromb. Haemostasis, Vol. 58, pp. 1017–1023 (1987), the disclosures of each of which are hereby incorporated herein by reference in their entirety. As those skilled in the art are aware, PAI-1 protein isolated from these sources exists chiefly as a latent form with a very low specific activity, as determined in tPA inhibition assays. This latent form can be further activated by treatment with denaturants such as sodium dodecyl sulfate (SDS), guanidium hydrochloride, and urea, or by treatment with negatively-charged phospholipids, as discussed in Hekman et al., J. Biol. Chem., Vol. 260, pp. 11581–11587 (1985), and Lambers et al., J. Biol. Chem., Vol. 262, pp. 17492–17496 (1987), the disclosures of each of which are hereby incorporated herein by reference in their entirety.

The literature is also replete with discussions of recombinant PAI-1 protein production, including, for example, such publications as Ginsburg et al., J. Clin. Invest., Vol 78, pp. 1673–1680 (1986), Ny et al., Proc. Natl. Acad. Sci. U.S.A., Vol. 83, pp. 6776–6781 (1986), Pannekoek et al., EMBO J., Vol. 5, pp. 2539–2544 (1986), Wun et al., FEBS Lett., Vol. 210, pp. 11–16 (1987), Alessi et al., Eur. J. Biochem., Vol. 175, pp. 531–540 (1988), and Andreasen et al., FEBS Lett., Vol. 209, pp. 213–218 (1986), the disclosures of each of which are hereby incorporated herein by reference in their entirety. Again, as described above with regard to naturally produced PAI-1 protein, latent recombinant PAI-1 protein forms may be further activated by treatment with denaturants or negatively-charged phospholipids.

As those skilled in the art are aware, PAI-1 protein may also be purchased from various commercial sources, such as, for example, from American Diagnostica Inc. (New York, N.Y.), where natural PAI-1 protein purified from human fibrosarcoma cells is available.

A particularly preferred source of PAI-1 protein is the recombinant PAI-1 protein expressed and purified in the manner described in Reilly et al., J. Biol. Chem., Vol. 265, No. 16, pp. 9570–9574 (1990), Sisk et al., Gene (Amst.), Vol. 96, pp. 305–309 (1990), and in the patent application Davis et al., U.S. Ser. No. 350,264, filed May 11, 1989, entitled "High Level Expression of Functional Human Plasminogen Activator Inhibitor in *E. coli*", the disclosures of each of which are hereby incorporated herein by reference in their entirety.

Another particularly preferred PAI-1 protein is PAI-1 protein which has been subjected to the process described in Hayman et al., U.S. Ser. No. 671,433, filed Mar. 20, 1991, entitled "Purification of Active and Inactive/Latent Forms of Plasminogen Activator Inhibitor-1", the disclosures of which are hereby incorporated herein by reference in their entirety. In accordance with the protocol set forth in the foregoing patent application, the active form of the PAI-1 protein can be separated from the inactive/latent form. Specifically, the processes described in the Hayman et al. patent application involve loading a sample containing a mixture of active and inactive/latent forms of PAI-1 on to a cation exchange resin of 10–50 micron particle size, and eluting the active and inactive/latent forms of PAI-1 into separate fractions using a mobile phase buffer with a gradient of increasing ionic strength or increasing pH, or both, under conditions where active and inactive/latent forms of PAI-1 are eluted from the resin in separate fractions. Other processes described therein involve loading a sample containing a mixture of active and inactive/latent forms of PAI-1 on to an anion exchange resin of 10–50 micron particle size, and eluting the active and inactive/latent forms of PAI-1 into separate fractions using a mobile phase buffer with a gradient of increasing ionic strength or decreasing pH, or both, under conditions where active and inactive/latent forms of PAI-1 are eluted from the resin in separate fractions.

The foregoing described and other known natural and recombinant PAI-1 protein sources and forms, as well as obvious variations thereof, are intended to fall within the ambit of the phrase "PAI-1 protein", as used herein.

As noted above, both recombinant and natural PAI-1 are known to exist in forms that differ in specific tPA inhibitory activity ("PAI-1 specific activity"), these two different forms being referred to herein as active and inactive/latent. The tPA inhibitory activity of active form PAI-1 is greater, generally much greater, than the tPA inhibitory activity of inactive/latent form PAI-1. Indeed, inactive/latent form PAI-1 has a low specific tPA inhibitory activity which is less than 5 units/ng, where a unit is defined as the amount of protein required to neutralize 1 international unit of tPA in an S2288 chromogenic assay. As used herein, the phrase "inactive/latent PAI-1 protein" denotes such low activity PAI-1 forms. Active form PAI-1 has a higher specific tPA inhibitory activity than inactive/latent form PAI-1, that is, an activity which is greater than 5 units/ng, generally greater than about 500 units/ng, where a unit is again defined as the amount of protein required to neutralize 1 international unit of tPA in an S2288 chromogenic assay. As used herein the phrase "active PAI-1 protein" denotes such higher activity PAI-1 forms. The S2288 assay is described in detail in the patent application Davis et al., U.S. Ser. No. 350,264, filed May 11, 1989, entitled "High Level Expression of Functional Human Plasminogen Activator Inhibitor in *E coli*", the disclosures of which are hereby incorporated herein by reference in their entirety. This assay measures the amidolytic activity of tPA on the chromogenic substrate D-Ile-Pro-Arg-NH-nitroanilide (S-2288), and the inhibition of this activity by PAI-1. In calculating inhibitory activity of PAI-1 in accordance with the S2288 assay, the activity of tPA is first expressed in IU by comparison with the International Reference Preparation for tPA. Then the calculation of inhibitory activity is carried out. For example, where a 50% inhibition of 10 IU of tPA activity is observed with $1.6 \times 10^{-3}$ mg/ml of PAI-1 in accordance with the S2288 assay, the specific activity of the PAI-1 protein inhibitor would be 0.03 units/ng. Similarly, where a 50% inhibition of 10 IU of tPA activity is observed with $1.7 \times 10^{-4}$ mg/ml of PAI-1 in accordance with the S2288 assay, the PAI-1 inhibitor would possess a specific activity of 0.3 units/ng. Although inactive and latent PAI-1 differ in that the tPA inhibitory activity of latent PAI-1 can be activated or stimulated, for example, by treatment with protein denaturants, whereas inactive PAI-1 cannot be activated in this manner, both inactive and latent PAI-1, with their low specific activity, are treated collectively herein, and are referred to herein as "inactive/latent PAI-1 protein".

In accordance with the present invention, the active form PAI-1 protein is stabilized. As earlier noted, the active form is by its nature unstable. This is particularly true at temperatures greater than 10° C., although stabilization problems have also been observed at lower temperatures. Thus, as used herein in accordance with the subject invention, by "stable", "stabilized" or "stabilizing", or variations thereof, it is meant the condition or process where the conversion of active form of PAI-1 protein to the inactive/latent form of PAI-1 protein is minimized (that is, is lessened). Generally, there is less than a 50% conversion from active form PAI-1 to inactive/latent form PAI-1, more often less than a 60% conversion from active to inactive/latent form PAI-1, and most often less than a 70% conversion from active to inactive/latent form PAI-1, such measurements being made at room temperature (i.e., at about 20° C.) and over a one week period. The preferable processes and compositions of the invention permit less than an 80% conversion from active to inactive/latent form PAI-1, and the most preferable processes and compositions of the invention permit less than a 90% conversion from active to inactive/latent form PAI-1, at room temperature over a one week period.

In accordance with the present invention, stabilization of active form PAI-1 protein may be accomplished by combining active form PAI-1 protein with a buffer having an ionic strength of at least about 5 millisiemens and a sugar selected from the group consisting of monosaccharides and disaccharides.

Buffers useful in the present invention include standard buffers compatible with proteins and such as, for example, ammonium carbonate, cacodylic acid, 4- or 5-hydroxymethylimidazole, pyrophosphoric acid, phosphoric acid, imidazole, 4- or 5-methylimidazole, triethanolamine, diethylbarbituric acid, 2,2-bis(hydroxymethyl)-2,2',2''-nitrilotriethanol, $KH_2PO_4$, N-tris(hydroxymethyl)methyl-2-aminoethanesulfonic acid ("TES"), N-2-hydroxyethylpiperazine-N'-2-ethanesulfonic acid ("HEPES"), triethanolamine, tris(hydroxymethyl)-aminomethane ("Tris"), N-tris(hydroxymethyl)-methylglycine ("Tricine"), N,N-bis(2-hydroxyethyl)glycine ("Bicine"), borax, glycine, ammonia(aqueous)/$NH_4Cl$, ethanolamine, succinate/succinic acid, and 2-(N-morpholino)ethanesulfonic acid ("MES"). Other suitable buffers will be readily apparent to one skilled in the art.

Preferably, the buffers have an ionic strength of at least about 5 millisiemens, more preferably between about 5 and about 50 millisiemens, even more preferably between about 8 and about 50 millisiemens. Most preferably, the ionic strength is between about 10 and about 15 millisiemens. As the foregoing indicates, the unit employed to denote ionic strength herein is millisiemens, which is also a unit of conductivity. As those skilled in the art will recognize, the conductivity of a buffered solution is a function of its ionic strength. The term millisiemens, employed herein in connection with ionic strength, thus refers to the buffer solution ionic strength, as measured by conductivity. All conductivity values referred to herein in units of millisiemens are measured at 24° C. in a 1 cm path length cell.

Compounds useful in the present invention as ionic strength contributors to the buffered solution (that is, to compounds for increasing buffered solution ionic strength) may include, but are not limited to, standard alkali metal salts commonly used in protein biochemistry, such as, for example, sodium chloride, sodium phosphate, and sodium ethylenediamine-tetraacetate. Such ionic strength contributors can optionally be included to increase the ionic strength of the buffered solution. Another useful ionic strength contributor is the amino acid arginine. Other suitable ionic strength contributors will be readily apparent to those skilled in the art. As the skilled artisan will recognize once armed with the present disclosure, such ionic strength contributors can be added to the buffer before addition of the buffer to the PAI-1 protein, sugar and/or other components, or after addition of the buffer to the PAI-1 protein, sugar and/or other components, the order of addition not being critical, and all such variations are intended to be within the scope of the present invention.

A particularly preferred buffer is a 150 mM sodium phosphate buffer.

Suitable stabilizing sugars include monosaccharides and disaccharides. Exemplary monosaccharides include glucose, fructose, arabinose, mannose, galactose, ribose, ribulose, xylose, xylulose, erythrose, erythrulose, threose, lyxose, allose, altrose, gulose, idose, and talose. Exemplary disaccharides include sucrose, lactose, maltose, isomaltose, and cellobiose. Other suitable stabilizing sugars will be readily apparent to those skilled in the art. Preferable stabilizing sugars include sucrose, fructose, and/or arabinose.

The amount of buffer, ionic strength contributor and sugar employed in the compositions and processes of the invention may vary widely, with the specific amount to be employed being well within the ambit of those skilled in the art. By way of general guidance, however, it is preferable to include in the stabilizing composition an amount of sugar which is between about 100 mM and about 1.5 M, more preferably between about 500 mM and about 1 M, although higher or lower amounts may be employed. Also by way of general guidance, the ionic strength contributor is best employed in an amount sufficient to bring the ionic strength of the buffer to at least about 5 millisiemens. Although the precise amount of ionic strength contributor to be added is dependent upon its inherent ability to contribute to ionic strength and the concentration of the buffer (i.e., the ionic strength contributed by the buffer), often about 100 mM to about 1.5 M of the ionic strength contributor, more preferably between about 150 mM to about 750 mM of the ionic strength contributor, will suffice.

A particularly preferred stabilizing composition of the present invention is a composition which employs sodium phosphate buffer, sucrose, arginine and sodium ethylenediaminetetraacetate, especially one which employs 150 μM sodium phosphate buffer (pH 8.6), 334 mM sucrose, 125 mM arginine and 25 mM sodium ethylenediaminetetraacetate.

In accordance with the present invention, stabilization of active form PAI-1 protein also may be accomplished by subjecting active PAI-1 protein to lyophilization. By the phrase "subjecting active PAI-1 protein to lyophilization", it is meant lyophilizing the protein in accordance with conventional lyophilization techniques. The protein may, if desired, be lyophilized in the presence of a variety of additional components suitable for lyophilization. Such additional components include, for example, buffers, ionic strength contributors, monosaccharide and disaccharide sugars, cryoprotectants, etc., as will be readily apparent to those skilled in the art in view of the present disclosures.

Exemplary and preferred buffers, ionic strength contributors and sugars are as described above. Suitable cryoprotectants include, for example, trehalose, glycerol, polyethylene glycol, sorbitol, dimethyl sulfoxide (DMSO), etc. Such cryoprotectants will assist in preventing damage to the PAI-1 protein potentially caused by an increased salt or sugar concentration and crystal formation during lyophilization, and thus are particularly useful in the present invention where salts and/or sugars are lyophilized with the PAI-1 protein. Such cryoprotectants are employed in minor amounts, such as, for example, about 0.1 to about 0.5 μg/ml.

In one preferable embodiment, the active PAI-1 protein subjected to lyophilization further comprises a sodium phosphate buffer. In another preferable embodiment, the protein subjected to lyophilization further comprises a buffer having an ionic strength of at least about 5 millisiemens and a sugar selected from the group consisting of monosaccharides and disaccharides, as described above.

Lyophilization, that is, the process involving the removal of water from a frozen sample by application of a vacuum (also frequently referred to as freeze-drying), may be carried out using standard lyophilization techniques well known to those skilled in the art. Briefly, the sample is first frozen, for example, in a dry ice and ethanol (or acetone) mixture at, for example, −80° C. The sample is then connected to a vacuum source, and a vacuum is applied, evaporating the moisture by sublimation. The rate of cooling due to evaporation of the solvent assists in maintaining the sample in the frozen state until moisture evaporation is completed. The result is a preserved dry protein sample. The dried sample is then generally sealed under vacuum and stored with refrigeration.

Prior to use, the lyophilized protein is generally reconstituted. Reconstitution may be carried out using any of a wide variety of different reconstitution liquids including, for example, deionized or distilled water, various buffers such as those described above, and various carriers or vehicles well known in the pharmaceutical industry, as well as other reconstitution liquids which will be readily apparent to those skilled in the art. For pharmaceutical applications, of course, the reconstitution liquid should be pharmaceutically acceptable. Pharmaceutically acceptable liquids are well known in the art, and are described, for example, in Remington's, Pharmaceutical Sciences, Gennaro, A. R., ed., Mack Publishing Co., Easton, Pa. (1985), and in The United States Pharmacopeia—The National Formulary, 22nd Revision, Mack Printing Company, Easton Pa. (1990), the disclosures of each of which are hereby incorporated herein by reference in their entirety.

The compositions of the invention comprising active PAI-1 protein in combination with a buffer having an ionic strength of at least about 5 millisiemens and a sugar selected from the group consisting of monosaccharides and disaccharides, and/or the active PAI-1 protein stabilized by lyophilization and then reconstituted, may be employed, if desired, as pharmaceutical compositions useful in methods for the treatment of inappropriate or excessive fibrinolysis, a physiological condition involving the undesired destruction of blood clots through the breakdown of fibrin. The pharmaceutical compositions of the invention, with their active PAI-1 protein component, serve to inhibit such fibrinolysis.

If desired, the pharmaceutical compositions of the invention may further comprise a carrier or vehicle. Such carriers and vehicles are well known in the art, and will be readily apparent to one skilled in the art. Suitable carriers and vehicles are described, for example, in Remington's, Pharmaceutical Sciences, Gennaro, A. R., ed., Mack Publishing Co., Easton, Pa. (1985), and in The United States Pharmacopeia—The National Formulary, 22nd Revision, Mack Printing Company, Easton Pa. (1990), the disclosures of each of which are hereby incorporated herein by reference in their entirety.

In carrying out the method of the invention, the mammal is most preferably a human. Administration may carried out in various fashions, such as intravascularly, intralymphatically, parenterally, subcutaneously, intramuscularly, intraperitoneally, interstitially, hyperbarically, or orally, using a variety of dosage forms. The useful dosage of PAI-1 to be administered (that is, the amount therapeutically effective to inhibit fibrinolysis), will vary depending upon such factors as the age, weight and mammal to be treated, the mode of administration, and the degree of fibrinolysis, as well as other factors which will be readily apparent to those skilled in the art, once armed with the present disclosures. Typically, dosage is initiated at lower levels and increased until the desired therapeutic effect is achieved. By way of guidance, however, generally between about 10 and about 50 μg/kg, preferably about 25 mg/kg, of the PAI-1 protein is administered. Of course, higher and lower amounts can be employed, the particular dosage to be employed being well within the ambit of those skilled in the art, in view of the subject disclosures.

As those skilled in the art will recognize, in carrying out the method of the invention, the pharmaceutical compositions may be administered alone or in combination with other therapeutic and/or diagnostic agents, as desired. Other such agents include, for example, thrombin and fibrinogen.

Kits useful for therapeutic applications comprising the pharmaceutical compositions of the present invention are also within the ambit of the present invention. Such pharmaceutical kits, which may be employed to inhibit fibrinolysis, may comprise a sterile container of a pharmaceutical composition of the invention. Alternatively, such pharmaceutical kits may comprise a sterile container of active PAI-1 protein, in lyophilized form, in an amount therapeutically effective to inhibit fibrinolysis, and at least one sterile container of a reconstitution liquid suitable for administration to said mammal.

Such kits may further include, if desired, one or more of various conventional pharmaceutical kit components, for example, one or more vehicles or carriers, one or more reconstitution liquids, one or more additional vials for mixing the PAI-1 protein, vehicles or carriers and any reconstitution liquid, etc., as will be readily apparent to those skilled in the art. Instructions, either as inserts or as labels, indicating quantities of the PAI-1 protein and vehicle or carrier, reconstitution liquid, etc., guidelines for mixing these components, and protocols for administration, may also be included in the kit.

Sterilization of the containers or any materials included in the kit may be carried out using conventional sterilization methodology well known to those skilled in the art. The sterile containers of PAI-1 protein, carrier or vehicle, and/or reconstitution liquid, for example, may comprise separate containers, or one or more multi-part containers (as exemplified by the Univial ™ two-part container available from Abbott Labs, Chicago, Ill.), as desired.

As those skilled in the art will recognize in view of the present disclosures, regardless of the source or form of PAI-1, it is preferable that the PAI-1 protein employed in preparing the compositions of the invention be substantially pure PAI-1, that is, the PAI-1 protein has less than about 5% impurities. This is especially true in the case of the pharmaceutical compositions of the invention. Most preferably the PAI-1 protein has less than about 1% impurities, that is, is purified to homogeneity.

In addition, not only is it preferable that the PAI-1 protein employed in preparing the compositions of the invention be substantially pure or purified to homogeneity, but as will be further recognized, it is most preferable that the substantially pure PAI-1 protein be substantially pure active PAI-1 protein, that is, the PAI-1 protein has less than about 5% inactive/latent PAI-1 protein. This, again, is especially true in the case of the pharmaceutical compositions of the invention. Preferably the PAI-1 protein has less than about 1% inactive/latent PAI-1 protein, that is, is purified to homogeneity.

The present invention is further described in the following examples. In the Examples 1-3, the active and inactive/latent forms were resolved as distinct peaks of elution using either anion or cation exchange chromatography, specifically a Pharmacia Mono-Q chromatography ion exchanger of 10 micro particle size, as described in Hayman et al., U.S. Ser. No. 671,433, filed Mar. 20, 1991, entitled "Purification of Active and Inactive/Latent Forms of Plasminogen Activator Inhibitor-1", the disclosures of which are hereby incorporated herein by reference in their entirety. Active form PAI-1 eluted under peak A and inactive/latent form PAI-1 eluted under peak C during ion exchange chromatography. The column fractions were diluted in an analysis buffer and analyzed directly for active PAI-1 protein (peak A) and inactive/latent PAI-1 protein (peak C), using a Hewlett Packard 1090 high pressure liquid chromatograph. The analytical chromatograms were integrated and the results were expressed as percent of initial peak A material remaining. The data was normalized to compensate for difference in injection volumes.

The following examples are provided for illustrative purposes and are not to be construed as limiting the scope of the appended claims.

EXAMPLE 1

Stabilization Of Active PAI-1 Protein By The Disaccharide Sucrose In Phosphate Buffer Purified PAI-1 (100 µl) was placed each of six 1 ml plastic Eppendorf vials. To four of the vials was added 100 µl of a solution containing 150 mM sodium phosphate buffer at pH 8.6 and the disaccharide sucrose in concentrations of 141 mM, 282 mM, 565 mM, and 1.13 M, respectively. For controls, 100 µl of a solution containing 150 mM sodium phosphate buffer at pH 8.6 with no sucrose was added two vials.

The solution in each of the four sucrose containing vials and one of the controls was carefully mixed and then incubated for 2 hours in a heating block at a temperature of 37° C. These vials were then cooled in an ice bath. The solution in the other control vial was carefully mixed and then cooled (without heating) in an ice bath.

All samples were analyzed directly for active PAI-1 protein (peak A area) and inactive/latent PAI-1 protein (peak C area). The results are shown in Table I. The results clearly illustrate the beneficial stabilizing effect of the disaccharide sucrose on active PAI-1 protein.

TABLE I

Effect Of Sucrose Concentration On Amount Of Active PAI-1 Protein (Peak A Area)

| Sample | Active PAI-1 (Peak A Area) | Inactive/Latent PAI-1 (Peak C Area) | % Initial Normalized To Control |
|---|---|---|---|
| Control No Heat No Sucrose | 920 | 486 | 100 |
| Control No Sucrose | 588 | 767 | 66 |
| Sucrose (141 mM) | 570 | 677 | 70 |
| Sucrose (282 mM) | 712 | 752 | 74 |
| Sucrose (565 mM) | 739 | 652 | 81 |
| Sucrose (1.13 M) | 830 | 754 | 80 |

Similar results were obtained after incubation at 4° C., but much longer sample incubation times were required.

EXAMPLE 2

Stabilization Of Active PAI-1 Protein By The Disaccharide Sucrose In Phosphate Buffer In Combination With Additional Ionic Strength Contributors Purified PAI-1 (100 µl) was placed each of six 1 ml plastic Eppendorf vials. To four of the vials was added 100 µl of a solution containing 150 mM sodium phosphate buffer at pH 8.6 and the disaccharide sucrose (334 mM) either alone or in combination with one or both of arginine (125 mM) and sodium ethylenediaminetetraacetate (EDTA) (25 mM). For controls, 100 µl of a solution containing 150 mM sodium phosphate buffer at pH 8.6 with no sucrose was added two vials.

The solution in each of the four sucrose containing vials and one of the controls was carefully mixed and then incubated for 2 hours in a heating block at a temperature of 37° C. These vials were then cooled in an ice bath. The solution in the other control vial was carefully mixed and then cooled (without heating) in an ice bath.

All samples were analyzed directly for active PAI-1 protein (peak A area) and inactive/latent PAI-1 protein (peak C area). The results are shown in Table II below. The results clearly illustrate the stabilizing effect of the disaccharide sucrose on active PAI-1 protein, and the further stabilizing effect provided by the additional ionic strength contributors.

TABLE II

Effect Of Various Ionic Strength Contributors In Combination With Sucrose In Phosphate Buffer On Amount Of Active PAI-1 Protein (Peak A Area)

| Sample | Active PAI-1 (Peak A Area) | Inactive/Latent PAI-1 (Peak C Area) | % Initial Normalized To Control |
|---|---|---|---|
| Control No Heat No Sucrose No Additional Ionic Strength Contributors | 986 | 335 | 100 |
| Control No Sucrose No Additional Ionic Strength Contributors | 658 | 727 | 64 |
| Sucrose (334 mM) | 752 | 672 | 71 |
| Sucrose (334 mM) Arginine (125 mM) | 759 | 446 | 84 |
| Sucrose (334 mM) EDTA (25 mM) | 725 | 474 | 81 |
| Sucrose (334 mM) Arginine (125 mM) EDTA (25 mM) | 956 | 459 | 91 |

EXAMPLE 3

Stabilization Of Active PAI-1 Protein By The Disaccharide Sucrose And The Monosaccharides Fructose and Arabinose In Phosphate Buffer Purified PAI-1 (100 µl) was placed in each of five 1 ml plastic Eppendorf vials. To three of the vials was added 100 µl of a solution containing 150 mM sodium phosphate buffer at pH 8.6, and one of the following sugars: the disaccharide sucrose (1.3 M); the monosaccharide fructose (2.2 M); or the monosaccharide arabinose (2.2 M). For controls, 100 µl of a solution containing 150 mM sodium phosphate buffer at pH 8.6 and no monosaccharide or disaccharide was added two vials.

The solution in each of the four sucrose containing vials and one of the controls was carefully mixed and then incubated for 2 hours in a heating block at a temperature of 37° C. These vials were then cooled in an ice bath. The solution in the other control vial was carefully mixed and then cooled (without heating) in an ice bath.

All samples were then diluted with an analysis buffer and analyzed directly for active PAI-1 protein (peak A area) and inactive/latent PAI-1 protein (peak C area). The results are shown in Table III below. The results clearly illustrate the stabilizing effect of the disaccharide sucrose and the monosaccharides fructose and arabinose on active PAI-1 protein.

TABLE III

Effect Of Sucrose, Fructose and Arabinose On Amount Of Active PAI-1 Protein (Peak A Area)

| Sample | Active PAI-1 (Peak A Area) | Inactive/Latent PAI-1 (Peak C Area) | % Initial Normalized To Control |
|---|---|---|---|
| Control No Heat No Sugar | 981 | 420 | 100% |
| Control No Sugar | 580 | 680 | 66% |
| Sucrose* (1.3 M) | 887 | 417 | 97% |
| Fructose (2.2 M) | 747 | 477 | 87% |
| Arabinose (2.2 M) | 657 | 476 | 83% |

*Starting PAI-1 only 70% peak A may explain higher stabilization by sucrose than seen above with more active initial PAI-1.

EXAMPLE 4

Ionic Strength Measurements For Various Solutions

Purified PAI-1 (100 µl) was placed each of six 1 ml plastic Eppendorf vials. To all of the vials was added 100 µl of a solution containing 150 mM sodium phosphate buffer at pH 8.6, and one or more of the following additional ionic strength contributors: NaCl (1 M or 0.375 M); arginine (1 M or 125 mM); sodium ethylenediaminetetraacetate (EDTA) (0.1 M or 25 mM). To one vial was also added sucrose.

The ionic strength of each solution was then determined by measuring the conductivity in a 1 cm path length at 24° C. using standard equipment. The results are shown below in Table IV below.

TABLE IV

Ionic Strength Of Various Sample Solutions

| Sample | Ionic Strength (Conductivity) |
|---|---|
| 150 mM phosphate, pH 8.6 | 10 millisiemens |
| 150 mM phosphate, pH 8.6 + 1 M NaCl | 82 millisiemens |
| 150 mM phosphate, pH 8.6 + 1 M Arginine | 22.5 millisiemens |
| 150 mM phosphate, pH 8.6 + 0.1 M EDTA | 24.5 millisiemens |
| 150 mM phosphate, pH 8.6 + 0.375 M NaCl | 42.5 millisiemens |
| 150 mM phosphate, pH 8.6 + | 13.5 millisiemens |

TABLE IV-continued

Ionic Strength Of Various Sample Solutions

| Sample | Ionic Strength (Conductivity) |
|---|---|
| 125 mM Arginine + 334 mM Sucrose + 25 mM EDTA | |

EXAMPLE 5

Stabilization Of Active PAI-1 Protein By Lyophilization

Recombinant PAI-1 protein was obtained in accordance with the protocol set forth in Reilly et al., J. Biol. Chem., Vol. 265, No. 16, pp. 9570–9574 (1990), Sisk et al., Gene (Amst.), Vol. 96, pp. 305–309 (1990), and in the patent application Davis et al., U.S. Ser. No. 350,264, filed May 11, 1989, entitled "High Level Expression of Functional Human Plasminogen Activator Inhibitor in *E. coli*", the disclosures of each of which are hereby incorporated herein by reference in their entirety. The PAI-1 protein was divided up into 1 ml aliquots containing either 1.56 ng or 3.125 ng PAI-1 in 1.8 ml vials, and the aliquots were then frozen.

Next, the frozen cryovials were placed in a lyophilization unit with loosened lids and lyophilized for 24 hours, using standard lyophilization techniques. The lids were tightened and the samples were stored at a temperature of −20° C.

To determine the activity of the PAI-1 protein, the lyophilized cryovials were taken from the freezer and allowed to warm to room temperature. Various aliquots were then reconstituted with 1 ml of deionized water on 11 different days over a period of 54 days, and the activity was measured using the S2251 chromogenic assay procedure set forth in the patent application Davis et al., U.S. Ser. No. 350,264, filed May 11, 1989, entitled "High Level Expression of Functional Human Plasminogen Activator Inhibitor in *E. coli*", the disclosures of which are hereby incorporated herein by reference in their entirety. In accordance with the S2251 chromogenic assay described therein, a unit of PAI-1 protein is the amount of protein required to neutralize 1 international unit of tPA in an S2251 chromogenic assay, where the enzymatic activity of tPA to generate plasmin from its plasminogen precursor is measured. The activity of tPA is expressed in IU by comparison with the International Reference Preparation for tPA. In essence, the S2251 assay measures the enzymatic ability of tissue plasminogen activator (tPA) to generate plasmin from its plasminogen precursor by determining the level of amidolytic activity of generated plasmin on the chromogenic substrate D-Val-Leu-Lys-p-nitroanilide (S2251). Thus, in this fashion, the inhibitory activity of PAI-1 is determined. As those skilled in the art will recognize that some variation in specific activity, e.g., in the range of ±10%, is to be expected.

The activity was reported as the percentage of the activity measured at day 0. The results are shown in Table V below. The results clearly illustrate the beneficial stabilizing effect of lyophilization on PAI-1 protein activity.

TABLE V

Effect Of Lyophilization On PAI-1 Protein Activity

| Day | 1.56 ng PAI-1 | 3.125 ng PAI-1 |
|---|---|---|
| 0 | 100.0 | 100.0 |
| 1 | 87.0 | 96.3 |
| 10 | 96.9 | 97.6 |
| 15 | 89.1 | 96.8 |
| 18 | 65.4 | 85.6 |
| 22 | 99.4 | 105.1 |
| 25 | 75.9 | 87.6 |
| 32 | 71.3 | 87.5 |
| 39 | 77.7 | 89.8 |
| 46 | 95.3 | 97.9 |
| 53 | 97.7 | 97.2 |

Various modifications of the invention, in addition to those shown and described herein, will be apparent to those skilled in the art from the foregoing description. Such modifications are also intended to fall within the scope of the appended claims.

What is claimed is:

1. A process for stabilizing active plasminogen activator inhibitor type-1 protein comprising combining said active plasminogen activator inhibitor type-1 protein with a buffer having an ionic strength of at least 5 millisiemens and a sugar selected form the group consisting of monosaccharides and disaccharides.

2. A process of claim 1 wherein said buffer is selected from the group consisting of ammonium carbonate, cacodylic acid, 4- or 5-hydroxymethylimidazole, pyrophosphoric acid, phosphoric acid, imidazole, 4- or 5-methylimidazole, triethanolamine, diethylbarbituric acid, 2,2-bis(hydroxymethyl)-2,2',2''-nitrilotriethanol, KH$_2$PO$_4$, N-tris(hydroxymethyl)methyl-2-aminoethanesulfonic acid, N-2-hydroxyethyl-piperazine-N'-2-ethanesulfonic acid, triethanolamine, tris(hydroxymethyl)-aminometane, N-tris(hydroxymethyl)-methylglucine, N,N-bis(2-hydroxyethyl)glycine, borax, glycine, ammonia(aqueous)/NH$_4$Cl, ethanolamine, succinate/succinic acid, and 2-(N-morpholino)ethanesulfonic acid, optionally in combination with an ionic strength contributor selected from the group consisting of sodium chloride, sodium phosphate, sodium ethylenediaminetetraacetate, and arginine.

3. A process of claim 1 wherein said ionic strength of said buffer is between 8 and 50 millisiemens.

4. A process of claim 3 wherein said ionic strength of said buffer is between 10 and 15 millisiemens.

5. A process of claim 1 wherein said sugar is a monosaccharide which is selected from the group consisting of glucose, fructose, arabinose, mannose galactose, ribose, ribulose, xylose, xylulose, erythrose, erythrulose, threose, lyxose, allose, altrose, gulose, idose, and talose.

6. A process of claim 1 wherein said sugar is a disaccharide which is selected from the group consisting of sucrose, lactose, maltose, isomaltose, and cellobiose.

7. A composition comprising active plasminogen activator inhibitor type-1 protein in combination with a buffer having an ionic strength of at least 5 millisiemens and a sugar selected from the group consisting of monosaccharides and disaccharides.

8. A composition of claim 7 wherein said buffer is selected from the group consisting of ammonium carbonate, cacodylic acid, 4- or 5-hydroxymethylimidazole, pyrophosphoric acid, phosphoric acid, imidazole, 4- or 5-methylimidizole, triethanolamine, diethylbarbituric acid, 2,2-bis(hydroxymethyl)-2,2',2''-nitrilotriethanol, KH$_2$PO$_4$, N-tris(hydroxymethyl(- methyl-2-aminoethanesulfonic acid, N-2-hydroxyethylpiperazine-N'-2-ethanesulfonic acid, triethanolamine, tris(hydroxymethyl)-aminomethane, N-tris(hydroxymethyl)-methylglycine, N,N-bis(2-hydroxyethyl)glycine, borax, glycine, ammonia(aqueous)/NH₄Cl, ethanolamine, succinate/succinic acid, and 2-(N-morpholino)ethanesulfonic acid, optionally in combination with an ionic strength contributor selected from the group consisting of sodium chloride, sodium phosphate, sodium ethylenediaminetetraacetate, and arginine.

9. A composition of claim 7 wherein said ionic strength of said buffer is between 8 and 50 millisiemens.

10. A composition of claim 9 wherein said ionic strength of said buffer is between 10 and 15 millisiemens.

11. A composition of claim 7 wherein said sugar is a monosaccharide which is selected from the group consisting of glucose, fructose, arabinose, mannose, galactose, ribose, ribulose, xylose, xylulose, erythrose, erythrulose, threose, lyxose, allose, altrose, gulose, idose and talose.

12. A composition of claim 7 wherein said sugar is a disaccharide which is selected from the group consisting of sucrose, lactose, maltose, isomaltose, and cellobiose.

* * * * *